United States Patent [19]

Grushkin et al.

[11] 3,965,049
[45] June 22, 1976

[54] ONE-STEP SYNTHESIS OF AROMATIC ORGANIC DISELENIDES

[75] Inventors: Bernard Grushkin, Pittsford, N.Y.; Michael N. Salzman, Winnetka, Calif.

[73] Assignee: Xerox Corporation, Stamford, Conn.

[22] Filed: May 20, 1974

[21] Appl. No.: 471,376

Related U.S. Application Data

[63] Continuation-in-part of Ser. No. 299,980, Oct. 24, 1972, abandoned.

[52] U.S. Cl. ............................... 260/2 M; 96/1 PC; 96/1.5; 260/239 R; 260/243 A; 260/248 CS; 260/250 R; 260/250 A; 260/251 R; 260/251.5; 260/267; 260/283 R; 260/296 D; 260/302 E

[51] Int. Cl.² ............... C08G 79/00; C07D 345/00; C07D 293/00

[58] Field of Search ............ 260/2 M, 607 R, 239 R

[56] References Cited
UNITED STATES PATENTS
3,671,467   6/1972   Gunther ............................ 260/2 M

*Primary Examiner*—Wilbert J. Briggs, Sr.
*Attorney, Agent, or Firm*—James J. Ralebate; James P. O'Sullivan; Jerome L. Jeffers

[57] ABSTRACT

Disclosed is a novel method for the preparation of aromatic organic diselenide compounds. The method involves reacting an alkali metal diselenide with certain halogenated aromatic compounds in dimethylformamide to form the corresponding aromatic diselenide. The use of dimethylformamide enables one to prepare certain aromatic diselenide compounds containing two replaceable halogen atoms in a one-step process.

5 Claims, No Drawings

ONE-STEP SYNTHESIS OF AROMATIC ORGANIC DISELENIDES

This application is a continuation-in-part of copending application Ser. No. 299,980 filed on Oct. 24, 1972, and now abandoned.

BACKGROUND OF THE INVENTION

This invention relates to a process for the introduction of selenium into aromatic molecules and more specifically, to a one-step process for the preparation of aromatic diselenide compounds.

Organic diselenides offer many advantages over elemental selenium in the method of manufacturing and use of electrophotographic plates and are advantageously employed as a photoconductive element in electrophotographic plates. Although aliphatic diselenides such as benzyl diselenide and polyselenide polymers are extensively used in electrophotography, the aromatic diselenides are preferred. Generally, the introduction of selenium into aliphatic and benzylic positions is accomplished by using a nucleophilic selenium reagent and by having a readily displacable group at these aliphatic or benzylic sites. For example, benzyl chloride can be reacted with sodium diselenide to form dibenzyl diselenide since the benzylic chlorine is in an activated position. Another method for the preparation of aromatic selenides involves the reaction of $K_2S_2$ with 1-chloroanthraquinone in alcohol to form di(anthraquinonyl-1) diselenide. This reaction will go fairly rapidly in alcohol due to the electron withdrawing nature of the oxygen atoms on the ring adjacent to the halogen bearing ring of the 1-chloroanthraquinone. However, aromatic halides in which the halogen is not in an activated position do not readily react with alkali metal diselenides. Thus, the preparation of aromatic diselenides from halogented aromatic compounds in which the halogen is bonded directly to the aromatic nucleus and which does not have a strong electron withdrawing group on the same ring or the ring adjacent to the halogen bearing ring has proven problematical. In order to achieve substitution when this type of aromatic halide is employed, an extremely active leaving agent, such as the diazonium group, must be used. In an alternative method, the insertion of elemental selenium into a Grignard reagent has been employed.

Several techniques for the preparation of aromatic diselenide polymers have been developed. One of the approaches is exemplified by the synthesis of phenylene diselenide polymers as illustrated by the following reactions:

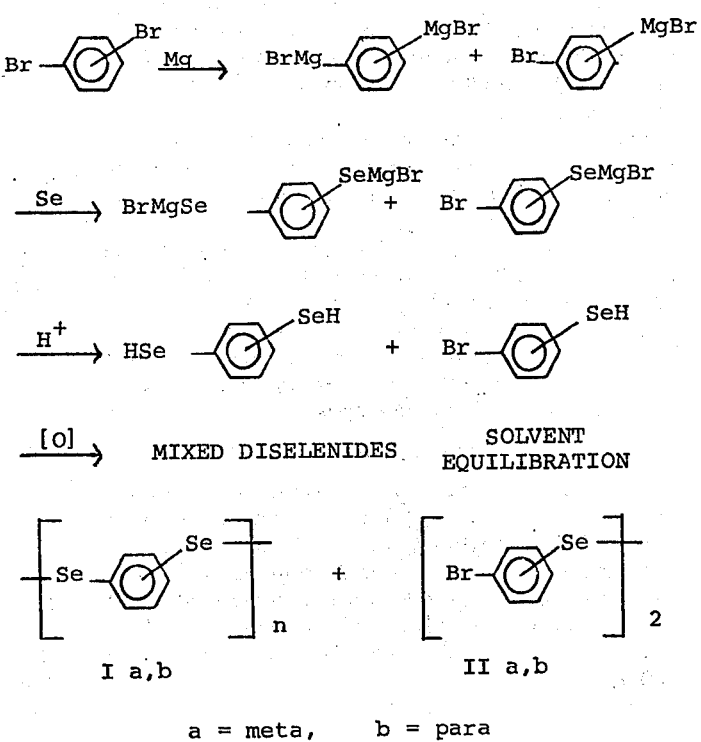

a = meta, b = para

One basis for introduction of selenium into the aromatic system is the well known reaction of the element with Grignard reagents. The obvious problem lies in the necessity to generate a double Grignard reagent. With the expected variability in the conversion efficiency, the air oxidation of the selenol and diselenol mixture yields a poorly defined mixture of diselenides.

Another general approach to the diselenide polymer synthesis is via intermeidate formation of phenylene bis-selenocyanates:

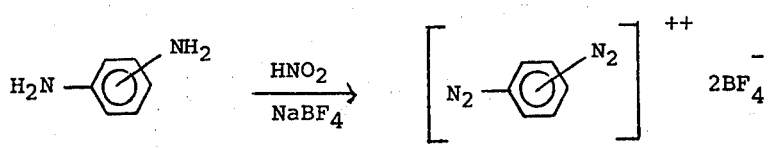

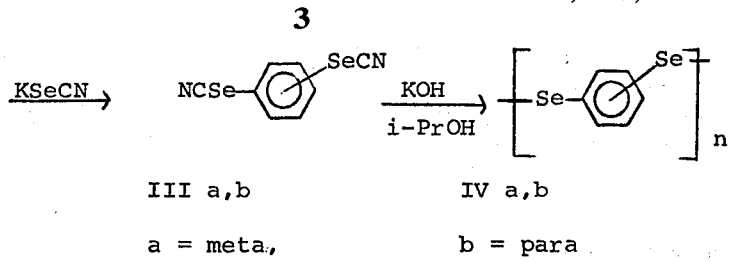

III a,b      IV a,b a = meta,      b = para

The alkaline hydrolysis of bis-selenocyanates is, of course, one way by which the earliest examples of aromatic diselenide polymers were produced.

From the examples given, the preparation of aromatic diselenide polymers until now has proven to be quite difficult in that several synthetic steps were required which are laborious and which require a great amount of time and expense. In addition, multi-step syntheses are restrictive and often produce a poor yield of the desired compound or polymer.

It would be desirable, and it is an object of the present invention, to provide a novel one-step process for the preparation of aromatic diselenide compounds.

A further object is to provide such a process in which the aromatic diselenide compound is an aromatic diselenide polymer.

Another object is to provide such a process wherein the aromatic diselenide compounds are prepared by the reaction of an alkali metal diselenide and an aromatic halide.

A further object is to provide such a process in which the reaction will proceed when the halogen on the aromatic halide is not in an activated state.

An additional object is to provide such a process in which the aromatic halide is reacted directly with the alkali metal diselenide without having first been converted to an intermediate composition.

SUMMARY OF THE INVENTION

The present invention is a process for the preparation of aromatic diselenide compounds which comprises reacting in dimethylformamide an alkali metal diselenide and a halogen substituted aromatic compound. The halogen substituted aromatic compound is selected from those aromatic halides which do not have strong electron withdrawing groups such as nitroso, NO; carboxylate,

ester,

oxo, =O; nitro, $NO_3$; and perfluoromethyl, $CF_3$, on the halogen bearing ring or on a ring adjacent to the halogen bearing ring. The reaction provides an aromatic diselenide compound, the organic portion of which corresponds to the non-halogen portions of the halogen substituted aromatic compound.

DETAILED DESCRIPTION

The above objects are accomplished in general by the discovery of the ability of a reagent consisting of alkali metal diselenide and dimethylformamide (DMF) to act as a nucleophilic displacement agent for halides that are substituted on an aromatic ring system. The process for the practice of the instant invention may be illustrated as follows:

$$2\,ArX + Se_2^{-2}/DMF \rightarrow (ArSe)_2 + 2X^- \qquad (1)$$

$$n\,XArX + nSe_2^{-2}/DMF \rightarrow +SeArSe+_n + 2nX^- \qquad (2)$$

wherein $n$ is a number greater than 1 and X is a halogen.

More specifically, the process of the present invention may be further illustrated by the following reactions:

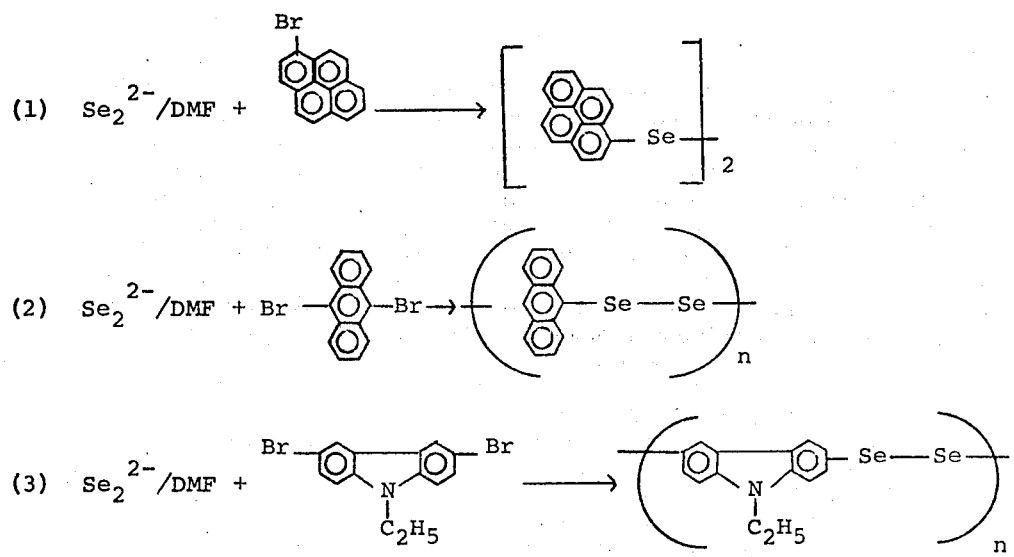

Any suitable halogenated aromatic compound having the halogen bonded directly to the aromatic nucleus may be used. Typical aryl radicals include compounds derived from such parent hydrocarbons as benzene, naphthalene, anthracene, tetracene, pentacene, phenanthrene, benz[a]anthracene, benzo[a]tetracene, benzo[a]pentacene, triphenylene, dibenz[a,c]anthracene, dibenzo[a,c]tetracene, dibenzo[a,c]pentacene, chrysene, trans-stilbene, dibenz[a,h]anthracene, dibenzo[a,j]tetracene, dibenzo[a,l]pentacene, benzo[a]phenanthrene, dibenz[a,j]anthracene, picene, pentaphene, perylene, benzo[g,h,i]perylene, coronene, biphenyl, m-terphenyl, diphenylene, o-terphenyl, benzo[g]chrysene, tribenz[a,c,j]anthracene, dibenzo[g,p]chrysene, benzo[c]chrysene, benzo[a]tetraphene, hexaphene, benzo[c]pentaphene, dibenzo[c,m-]pentaphene, naphtho[2,3-c]pentaphene, benzo[a]perylene, dibenzo[a,j]perylene, dibenzo[a,n]perylene, dibenzo[b,pqr]perylene, tribenzo[b,k,pqr]perylene, dibenzo[b,k]perylene, benzo[tuv]bisanthene, benzo[j]terylene, pyrene, benzo[c]-pyrene, benzo[a]pyrene, dibenzo[b,e]pyrene, dibenzo[a,w]pyrene, dibenzo[e,l]pyrene, dibenzo[a,h]pyrene, dibenzo[a,i]pyrene, naphtho[2,3-e]pyrene, naphtho[ ,3-a]pyrene, dinaphtho[2,3-a:2′,3′-h]pyrene dinaphtho[2,3-a:2′,3′-i]pyrene, tribenzo[a,e,i]pyrene, peropyrene, dibenzo[e,p]peropyrene, anthanthrene, dibenz[a,j]anthanthrene, dibenz[a,k]anthanthrene, azulene, p-terphehyl, fluorene, acenaphthylene, acenaphthene, benzo[c]tetraphene, toluene, m-xylene, mesitylene, durene and other substituted aromatic organic compounds. Typical examples may include dichlorobenzene, p-dichlorobenzene, m-dibromobenzene, m-difluorobenzene, dibromonaphthalene, diiodonaphthalene; dibromoanthracene; diiodobenzene and its analogs, dibromocarbazole and dibromopyrene.

Likewise, suitable heterocyclic compounds which are aromatic in nature may be used. Typical examples include heterocyclic radicals derived from such parent compounds as furans, pyridines, such as dibromopyridine, thiophenes, benzothiazole, imidazolines and triazines such as 2,4,6-trichlorotriazine. The hetero atom can be selected from oxygen, nitrogen and sulfur. Also heterocyclic divalent radicals can be the organic portion of the compounds of this invention derived from radicals such as thienyl, benzothienyl, naphthothienyl, selenophenyl, benzoselenophenyl, naphthoselenophenyl, thianthrenyl, selenanthrenyl, furyl, pyranyl, isobenzofuranyl, chromenyl, xanthenyl, selenoxanthenyl, phenoxathiinyl, pyrrolyl, imidazolyl, pyrazolyl, pyridyl, pyrimidinyl, pyridazinyl, indolizinyl, isoindolyl, indolyl, indazolyl, pyrinyl, quinolizinyl, isoquinolyl, quinolyl, phthalazinyl, naphthyridinyl, quinoxalinyl, quinazolinyl, cimnolinyl, pteridinyl, carbazolyl, carbolinyl, phenanthridinyl, acrydinyl, perimidinyl, phenanthrolinyl, phenazinyl, phenariazinyl, thiazolyl, selenazolyl, phenothiazinyl, phenoselenazinyl, phenoxazinyl, triazolyl and other heterocyclic radicals.

More specifically and by way of illustration, the process according to the present invention comprises providing sodium diselenide which may be prepared by any conventional technique such as suspending 17.38 grams of selenium in 200 milliliters of liquid ammonia under positive pressure at a temperature of −40° to −50°C. under normal atmospheric pressure and slowly adding thereto small pieces of sodium to form disodium diselenide which is prepared in the manner described in Rec. Trav. Chem. Pays-Bas, 81, 58 (1962) and the same publication at 83, 208 (1964) all of which is incorporated herein by reference.

After addition, the suspension is stirred for one hour and ammonia is removed by allowing the reaction vessel to slowly warm up and passing purified nitrogen over it. Thereafter, 33.60 grams of 9,10-dibromoanthracene is added along with 250 milliliters of dimethylformamide and the mixture is heated slowly under a stream of nitrogen in a mantle until the appearance of the diselenide polymer in the form of a red precipitate is noticed at 105°C. The temperature is kept at about 105°C. to 110°C. for an additional 2 hours. The precipitate is filtered and carefully washed with cold DMF. After drying, the solid is suspended in 200 milliliters of ethanol and 25 milliliters of 2N HCl. Bubbling is noticed as the suspension is stirred at room temperature for ½ hour. The product is filtered, washed with alcohol and water and dried to yield 28.4 grams of product (85% of theory) having a melting point of 320°C.

The reaction of sodium diselenide with aromatic halides in which the halogen is not activated is at best very sluggish in other solvents, e.g., nitrobenzene, requiring exceedingly long periods of time and high temperatures to obtain only a small amount of product. On the other hand, the reaction is readily carried out using the reagent mixture of DMF and alkali diselenide. Although the role of DMF in the reaction mixture is not fully understood, it is believed that in the presence of DMF the diselenide dianion acts as an exceptionally strong nucleophile to displace halogen from the aromatic nucleus. The compounds produced according to the process of this invention are photoconductive. Accordingly, the photoconductive materials can be employed in electrostatic copying plates useful in the electrophotographic process as disclosed in U.S. Pat. No. 3,671,467.

The following examples are given to enable those skilled in the art to more clearly understand and practice the invention. They should not be considered as a limitation upon the scope of the invention, but merely as being illustrative thereof.

EXAMPLE I

Sodium (2.3 grams) is slowly added under nitrogen to a suspension of 7.9 grams of selenium in 250 milliliters of liquid ammonia at −40°C. After addition, the solution is stirred for 1 hour after which the ammonia is allowed to evaporate by allowing the temperature to rise slowly. Dimethylformamide (200 milliliters) and 30.24 grams of bis-9,10 dibromoanthracene are added to the above reagent and the mixture is slowly heated to 115°C. At 80°C. a blue solution appears and as the temperature reaches 105°C. a red solid precipitats. The precipitate is filtered and washed with dimethylformamide and hot benzene and is extracted in a soxhlet extractor with benzene for 48 hours. A yield of 14.1 grams is obtained which melts at approximately 320°C. The filtrate is diluted with methanol to yield 12.2 grams of an orange product which softens at 221°C. and melts at approximately 310°C. The precipitate is shown to be (anthracene-bis-9,10-diselenide polymer) by elemental analysis the results of which appear below.

Calculated: carbon 50.30%, hydrogen 2.40% and selenium 47.31%. Found: carbon 50.25%, hydrogen 2.41% and selenium 47.50%.

EXAMPLE II

The reaction according to Example I is repeated with the exception that 3bromopyrene is substituted for the di-bromoanthracene to provide bis(3-pyrenyl)diselenide.

EXAMPLE III

The reaction according to Example I is repeated with the exception that 3,6-dibromo-N-ethylcarbazole is substituted for the di-bromoanthracene to provide poly-3,6-[N-ethyl carbazole] diselenide carbazolyl.

EXAMPLE IV

The reaction according to Example I is repeated with the exception that bis-4,4'-dibromoazobenzene is substituted for di-bromoanthracene. Elemental analysis reveals the material to be (bis-4,4'-diselenoazobenzene) the results of which appear below.

Calculated: carbon 42.60%, hydrogen 2.37%, nitrogen 8.28% and selenium 46.75%. Found: carbon 40.38%, hydrogen 2.42%, nitrogen 7.70% and selenium 48.53%.

EXAMPLE V

The reaction according to Example I is repeated with the exception that di-bromoanthanthrone is substituted for the di-bromcanthracene. Elemental analysis of the product reveals the material to be (diselenoanthanthrone) the results of which appear below.

Calculated: carbon 57.14%, hydrogen 1.73%, selenium 24.20%, and oxygen 6.92%. Found: carbon 54.65%, hydrogen 1.88%, selenium 33,30% and oxygen 8.91%.

Although the present examples are specific in terms of conditions and materials used, other materials may be added into the reaction mixture to increase the speed of reaction or conditions may be altered in order to facilitate the reaction.

Anyone skilled in the art will have other modifications occur to him based on the teachings of the present invention. These modifications are intended to be encompassed within the scope of this invention.

What is claimed is:

1. A method for the formation of aromatic diselenide compounds which comprises reacting in dimethylformamide an alkali metal diselenide and halogen substituted aromatic compound containing two replaceable halogen atoms and having no strong electron withdrawing groups other than halogen on the halogen bearing ring or on a ring adjacent to the halogen bearing ring, to thereby form an aromatic diselenide compound, the organic portion of which corresponds to the non-halogen portions of the halogen substituted aromatic compound.

2. The method of claim 1 wherein the halogen substituted aromatic compound is bis-3,6-dibromo-N-ethylcarbazole and the product is poly-3,6(N-ethylcarbazoleyl) diselenide.

3. The method of claim 1 wherein the halogen substituted aromatic compound is dibromoanthracene and the product is anthracene-bis-9,10 diselenide polymer.

4. The method of claim 1 wherein the halogen substituted aromatic compound is bis-4,4'-dibromoazobenzene and the product is bis-4,4'-diselenoazobenzene.

5. The method of claim 1 wherein the halogen substituted aromatic compound is di-bromoanthanthrone and the product is diselenoanthanthrone.

* * * * *

UNITED STATES PATENT AND TRADEMARK OFFICE
CERTIFICATE OF CORRECTION

PATENT NO. : 3,965,049
DATED : June 22, 1976
INVENTOR(S) : Bernard Grushkin and Michael N. Salzman It is certified that error appears in the above-identified patent and that said Letters Patent are hereby corrected as shown below:

Under "Attorney, Agent, or Firm", "James J. Ralebate" should be corrected to read --James J. Ralabate--.

In line 4 of the Abstract, after "compounds" insert --containing two replaceable halogen atoms--.

In line 7 of the Abstract, delete "containing two replaceable halogen atoms" after the word "compounds".

Column 2, line 59, "intermeidate" should be corrected to read --intermediate--.

Column 6, line 53, "precipitats" should be corrected to read --precipitates--.

Column 7, line 1, "3bromopyrene" should be corrected to read --3-bromopyrene--.

Column 7, line 26, "di-bromcanthracene" should be corrected to read --di-bromoanthracene--.

Column 7, line 31, "33,30%" should be corrected to read --33.30%--.

Signed and Sealed this

Fourteenth Day of September 1976

[SEAL]

Attest:

RUTH C. MASON
*Attesting Officer*

C. MARSHALL DANN
*Commissioner of Patents and Trademarks*